US00PP33193P2

(12) United States Plant Patent
Smit

(10) Patent No.: US PP33,193 P2
(45) Date of Patent: Jun. 22, 2021

(54) ***ALOE* PLANT NAMED 'EC-ALAC-2003'**

(50) Latin Name: *Aloe aculeata*
Varietal Denomination: EC-ALAC-2003

(71) Applicant: Eden Collection, BV, Sappemeer (NL)

(72) Inventor: Obed Smit, Sappemeer (NL)

(73) Assignee: Eden Collection B.V.

( * ) Notice: Subject to any disclaimer, the term of this patent is extended or adjusted under 35 U.S.C. 154(b) by 0 days.

(21) Appl. No.: 17/036,678

(22) Filed: Sep. 29, 2020

(51) Int. Cl.
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 6/00
See application file for complete search history.

(56) References Cited

PUBLICATIONS

UPOV hit on *Aloe* plant named, 'EC-ALAC-2003', QZ PBR 20200908, filed Mar. 31, 2020.*

* cited by examiner

*Primary Examiner* — Anne Marie Grunberg
(74) *Attorney, Agent, or Firm* — Cassandra Bright

(57) ABSTRACT

A new and distinct cultivar of *Aloe* plant named 'EC-ALAC-2003' is disclosed, characterized by leaves with distinctive raised yellow-green oblong ridges and a serrate light red and yellow-green margin. Foliage is attractively tapered and slightly arching. The new variety is an *Aloe*, typically produced as an indoor or outdoor ornamental plant.

3 Drawing Sheets

Latin name of the genus and species: *Aloe aculeata.*
Variety denomination: 'EC-ALAC-2003'.

BACKGROUND OF THE INVENTION

The new cultivar is a product of a planned breeding program. The seed parent an unpatented proprietary *Aloe aculeata* hybrid referred to as '12AL-44'. The pollen parent an unpatented proprietary *Aloe aculeata* hybrid referred to as '12AL-47'. The crossing was made during 2013 in Sappemeer, The Netherlands at a commercial greenhouse. 'EC-ALAC-2003' was discovered by the inventor in 2014.

Asexual reproduction of the new cultivar 'EC-ALAC-2003' was first performed in Sappemeer, The Netherlands, at a commercial laboratory by tissue culture in September of 2014. 'EC-ALAC-2003' has since produced several generations and has shown that the unique features of this cultivar are stable and reproduced true to type.

SUMMARY OF THE INVENTION

The cultivar 'EC-ALAC-2003' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-ALAC-2003.' These characteristics in combination distinguish 'EC-ALAC-2003' as a new and distinct *Aloe* cultivar:

1. Distinctive raised oblong ridges colored Yellow-Green 193B.
2. Serrate light red and yellow-green margin.
3. Attractively tapered and slightly arched foliage.

PARENTAL COMPARISON

Plants of the new cultivar 'EC-ALAC-2003' are similar to the seed parent in most horticultural characteristics. However, plants of the new variety differ from the seed parent in the following:

1. New cultivar has a light red serrate margin, the seed parent does not have a colored margin.
2. The new variety has distinctly raised stripes, the seed parent has stripes which are not raised.
3. The new variety has a thicker leaf base than the seed parent.

Plants of the new cultivar 'EC-ALAC-2003' are similar to the pollen parent in most horticultural characteristics. However, plants of the new variety differ in the following:

1. New cultivar has a light red serrate margin; the pollen parent has a red margin.
2. Foliage of the new variety is more acutely tapered.
3. The new variety has distinctly raised stripes, the pollen parent has stripes which are not raised.

COMMERCIAL COMPARISON

'EC-ALAC-2003' can be compared to the unpatented commercial variety *Aloe* 'Spider'. The two *Aloe* varieties are similar in most horticultural characteristics; however, the new variety differs in the following:

1. Plants of the new variety have a rosette formation; plants of this comparator form multiple growth points.
2. The new variety has distinctly raised stripes, this comparator has stripes which are not raised.
3. This comparator does not have the serrate light red margin of the new variety.

'EC-ALAC-2003' can also be compared to the commercial variety *Aloe* 'EC-ALOE-1801', U.S. Plant Pat. No. 31,336. The two *Aloe* varieties are similar in most horticultural characteristics; however, the new variety differs in the following:

1. New cultivar has light red marginal serrations, this comparator has darker red and thicker marginal serration.
2. The new variety has dark green foliage with many light green stripes, foliage of this comparator is solid green.

BRIEF DESCRIPTION OF THE PHOTOGRAPHS

The accompanying photograph in FIG. 1 illustrates in full color a typical plant of 'EC-ALAC-2003' grown in a greenhouse in Sappemeer, The Netherlands. This plant is approximately 11 months old, shown in a 10.5 cm container.

Figure 1:
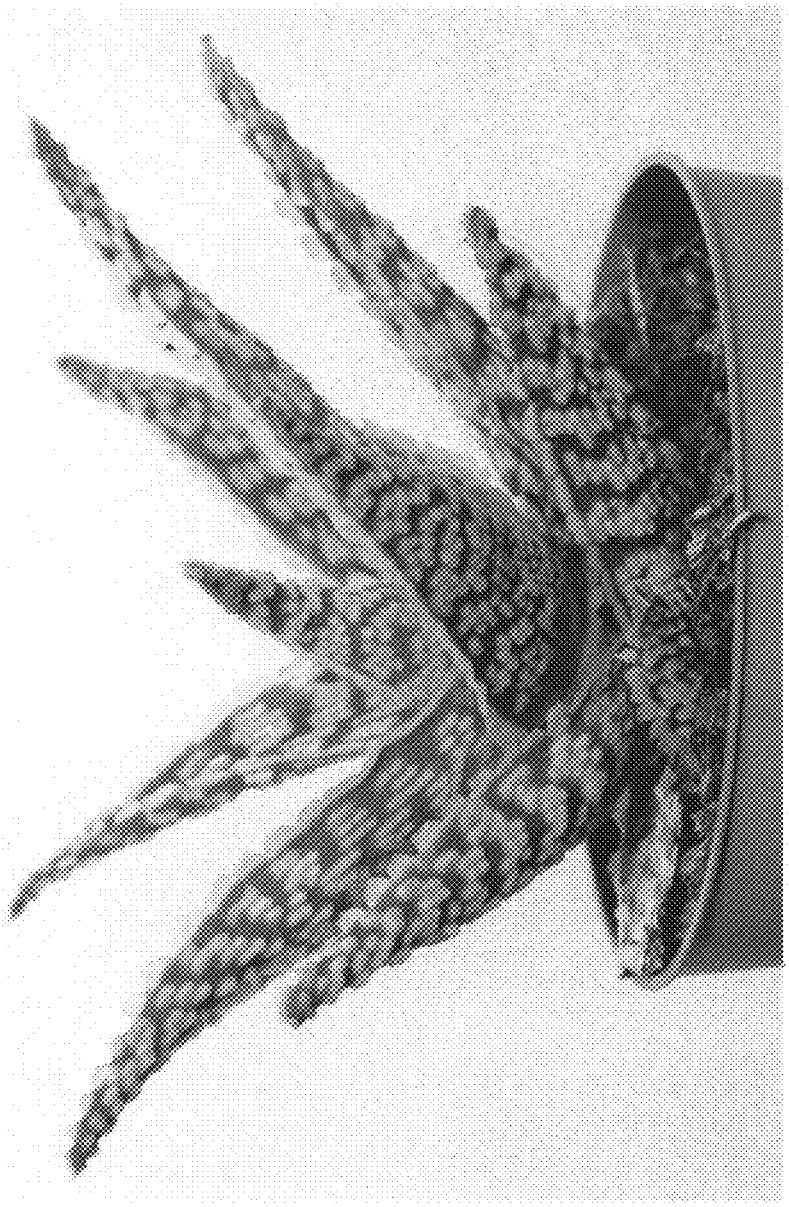
Figure 2:
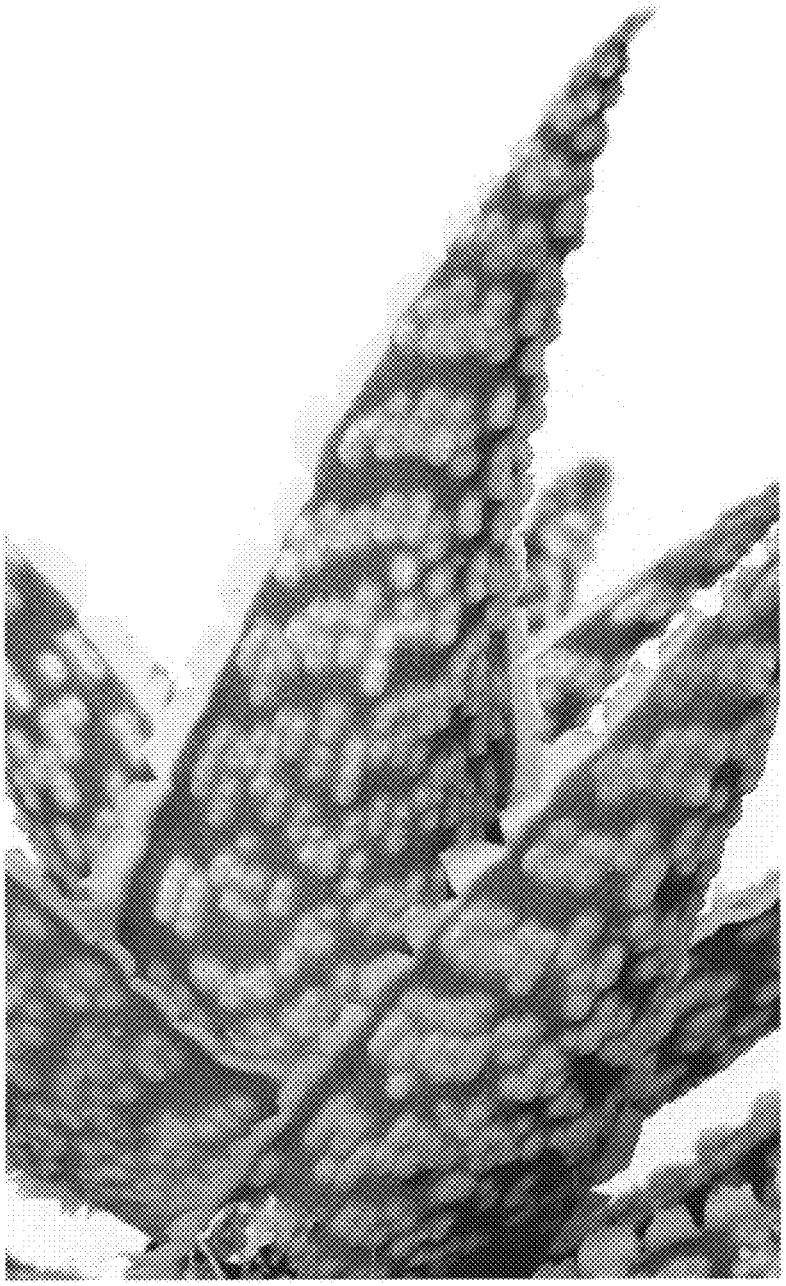
FIG. 2 illustrates a close up view of the underside of the foliage.
Figure 3:
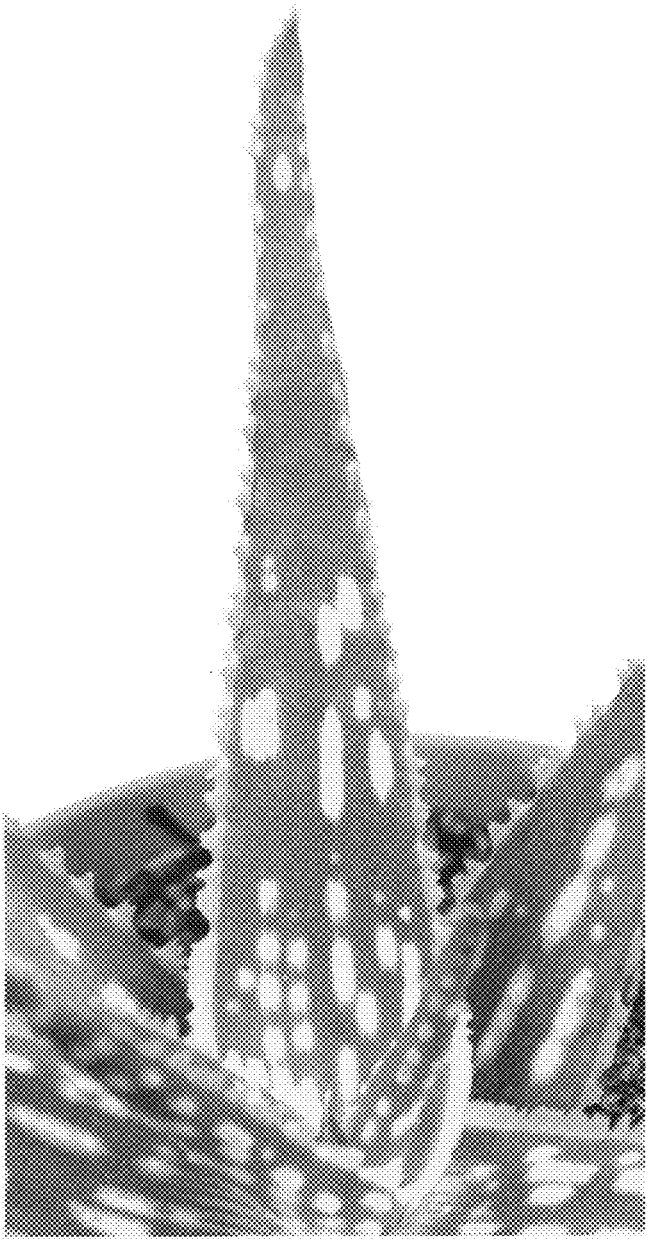
FIG. 3 illustrates a close up view of the upperside of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2015 edition, except where general terms of ordinary dictionary significance are used. The following observations and measurements describe 'EC-ALAC-2003' plants in a commercial greenhouse in Sappemeer, The Netherlands during April. Temperatures ranged from 21° C. to 25° C. during the day, and 18° C. to 21° C. during the night. No artificial light, photoperiodic treatments or chemical treatments were given to the plants. Natural light conditions were approximately 2500 to 3000 fc of light. Measurements and numerical values represent averages of typical plant types.

Botanical classification: *Aloe* hybrid 'EC-ALAC-2003'.

Age of the plant described: 11 months in a 10.5 cm pot.

PROPAGATION

Time to initiate roots: Approximately 7 to 10 days at 20° C.

Time to produce a rooted liner: About 28 to 35 days at 20° C.

Propagation method: Tissue culture.

PLANT

Growth habit: Basal rosette composed of slightly arching, tapered leaves.

Container size: 10.5 cm.

Height: 10.2 cm to top of foliar plane.

Plant spread: Average 14.6 cm.

Growth rate: Low to moderate.

Branching characteristics: Single basal rosette. No branches.

Root description: Moderately dense, fibrous. White, around RHS 155A.

FOLIAGE

Leaf:

*Arrangement.*—Rosette.

*Quantity of leaves.*—Approximately 15 per rosette.

*Average length.*—9.3 cm.

*Average width.*—3.3 cm.

*Average thickness.*—0.9 cm.

*Shape of blade.*—Tapering lanceolate, succulent.

*Apex.*—Long acuminate.

*Base.*—Broad cuneate.

*Margin.*—Coarsely dentate-serrate. Average length of teeth: 0.2 cm, average width of teeth: 0.3 cm, colored Yellow-Green 145B and 145C, serration margin near Red 37B.

*Aspect.*—Slightly concave.

*Texture of upper surface.*—Pustulate, visible as narrow oblong ridges colored Yellow-Green 145A and 145B occasionally tinged Red 37B and 37C at top of ridge. Average length of ridges: 0.4 cm, average diameter of ridges: 0.175 cm, average height of ridges: 0.15 cm.

*Texture of under surface.*—Pustulate, visible as narrow oblong dots colored Yellow-Green 145B and 145C. Average length of ridges: 0.15 cm, average diameter of ridges: 0.15 cm, average height of ridges: 0.05 cm.

*Appearance upper surface.*—Slightly glossy.

*Appearance under surface.*—Slightly glossy.

*Color.*—Young foliage upper side: Near Green 137A fading lighter towards the base; 143B and 143C. Oblong ridges colored Yellow-Green 145A and 145B occasionally tinged Red 37B and 37C at top of ridge. Margin near Yellow-Green 145B and 145C, serration margin near Red 37B. Young foliage under side: Near Green 137A fading lighter towards the base; 143B and 143C. Oblong ridges colored Yellow-Green 145A and 145B. Margin near Yellow-Green 145B and 145C, serration margin near Red 37B. Mature foliage upper side: Near RHS Green; NN137B tinged Yellow-Green 147A, fading lighter towards the base; near Green NN137C. Oblong ridges colored Yellow-Green 145A and 145B occasionally tinged Red 37B and 37C at top of ridge. Margin near Yellow-Green 145B and 145C, serration margin near Red 37B. Mature foliage under side: Near RHS Green; NN137C tinged N138B, fading lighter towards Green 137D. Oblong ridges colored Yellow-Green 145A and 145B. Margin near Yellow-Green 145B and 145C, serration margin near Red 37B.

Venation: Parallel venation, coloration indistinguishable from leaf blade.

FLOWER

Flowering: Not observed.

OTHER CHARACTERISTICS

Seeds and fruits: None observed to date.

Temperature tolerance: Tolerates temperatures up to 40 degrees C.

Disease/pest resistance: Neither resistance nor susceptibility to normal diseases and pests known to *Aloe* observed to date.

What is claimed is:

1. A new and distinct cultivar of *Aloe* plant named 'EC-ALAC-2003' as herein illustrated and described.

* * * * *